United States Patent
Franzen

[11] Patent Number: 5,719,392
[45] Date of Patent: Feb. 17, 1998

[54] METHOD OF MEASURING ION MOBILITY SPECTRA

[75] Inventor: Jochen Franzen, Bremen, Germany

[73] Assignee: Bruker Saxonia Analytik GmbH, Bremen, Germany

[21] Appl. No.: 637,199

[22] Filed: Apr. 24, 1996

[30] Foreign Application Priority Data

Apr. 26, 1995 [DE] Germany .................. 195 15 270.0

[51] Int. Cl.$^6$ .................................................. H01J 49/40
[52] U.S. Cl. .................................... 250/282; 250/287
[58] Field of Search ................................ 250/282, 287, 250/281

[56] References Cited

U.S. PATENT DOCUMENTS

| | | | |
|---|---|---|---|
| 4,633,083 | 12/1986 | Knorr et al. | 250/282 |
| 4,707,602 | 11/1987 | Knorr | 250/282 |
| 5,331,158 | 7/1994 | Dowell | 250/287 |
| 5,367,162 | 11/1994 | Holland et al. | 250/287 |
| 5,371,364 | 12/1994 | Davies et al. | 250/287 |
| 5,396,065 | 3/1995 | Myerholtz et al. | 250/287 |

FOREIGN PATENT DOCUMENTS 1288493  9/1972  United Kingdom.

OTHER PUBLICATIONS

F.J. Knorr et al., Fourier Transform Ion Mobility Spectrometry, Analytical Chemistry, vol. 57, No. 2, pp.402–406, Feb. 1985.

F.J. Knorr, Fourier Transform Time–of–Flight Mass Spectrometry, Analytical Chemistry, vol. 58, No. 4, pp.690–694, Apr. 1986.

M. Misakian et al., Drift tubes for characterizing atmospheric ion mobility spectra using ac, ac–pulse, and pulse time–of–flight measurement techniques, Rev. Sci. Instrum., vol. 60, No. 4, pp. 720–729, Apr. 1989.

Primary Examiner—Jack I. Berman
Assistant Examiner—Kiet T. Nguyen

[57] ABSTRACT

A method for measuring the mobility spectra of ions with ion mobility spectrometers (IMS). The method consists of impressing upon the essentially continuous ion flow of an IMS ion source, which comprises various ion types with various mobilities, a temporal switching signature with an ion admission of approximately 50% by using a very fast ion flow switch, whereby the signatures for the various ion types are displaced toward each other in different manners during the operating time due to the different velocities. From the quasi-continuously received ion current signal at the end of the path of the ion mobility spectrometer the composition of the ion types can be recovered according to mobility and intensity by decoding the switching signature. At the same time an improvement in resolution can be achieved by deconvolution of the diffusion profile. The method has a high duty cycle for the substance admitted and for the ions of ion flow.

10 Claims, 2 Drawing Sheets

METHOD OF MEASURING ION MOBILITY SPECTRA

The invention relates to a method for measuring the mobility spectra of ions with ion mobility spectrometers (IMS).

The invention consists of impressing upon the essentially continuous ion flow of an IMS ion source, which comprises various ion types with various mobilities, a temporal switching signature with an ion admission of approximately 50% by using a very fast ion flow switch, whereby the signatures for the various ion types are displaced toward each other in different manners during the operating time due to the different velocities. From the quasi-continuously received ion current signal at the end of the path of the ion mobility spectrometer the composition of the ion types can be recovered according to mobility and intensity by decoding the switching signature. At the same time an improvment in resolution can be achieved by deconvolution of the diffusion profile. The method has a high duty cycle for the substance admitted and for the ions of ion flow.

PRIOR ART

Ion mobility spectrometers are normally operated with very short pulses of ion current. The ions are generated continuously in an ion source and then admitted to the drift section of the spectrometer by a switchable grid. The time spans for ion admittance are usually 100 to 300 microseconds and total scanning takes 30 to 50 milliseconds.

The ions admitted through the grid are then drawn through the drift section by an axially oriented electric field, whereby its velocity, from which the mobility can be calculated, depends on the size of the ions and on shape factors. At the end of the drift section the ion current arriving is measured by an ion detector quasi-continuously, digitized, and stored. Evaluation of the spectrum provides information about the velocities of the ions involved and hence an indication of the substances involved. The method is exceptionally sensitive for certain groups of substances and is therefore chiefly used for measuring pollutants in air, e.g. for monitoring chemical laboratories, for continuous monitoring of filters, for controlling drying processes, for waste air monitoring and the like.

All ions with the same charge are subject to the same force of traction through the electric field. Ions with different cross sections show different drift velocities, whereby the cross sections are essentially dependent on the masses, and to a lesser extent on the special shapes of the molecules. Measurement of the drift velocity in an ion mobility spectrometer can therefore be used for an approximate determination of ion masses. If ions with different charges are present, the drift velocity leads to a determination of mass-to-charge ratios.

The grid switching process serves as a starting pulse for the measurement of drift velocity. Due to the diffusion of the ions in the forward and reverse directions a diffusion profile is generated during the drift This produces approximately a bell-shaped Gaussian distribution curve for the ion signals along the time axis. Drift velocity is determined from the measured drift time at the center of the bell-shaped curve and the known length of the drift section in the drift tube of the spectrometer.

The ions are usually generated by the bombardment with electrons from a beta emitter, e.g. $Ni^{63}$. Corona discharges and UV lamps are also in use for this purpose.

At a normal scan repetition rate of 25 spectra per second and an ion admission time of 200 microseconds the duty cycle for the utilization of the ions of a substance is only 0.5%. The remaining ions are discharged, which chiefly takes place in the switchable grid, and are lost to the measuring process.

F. J. Knorr et al. (Anal. Chem. 1985, 57, 402) described a method which uses a rather continuous axial ion beam, modulated by two barrier grids. The first barrier grid is positioned directly behind the ion source and the second one directly in front of the ion detector. Due to a synchronous modulation of the two grids an interference pattern of the ion beam is generated, whereby some ion types can pass whilst others are held back by the interterence of their drift time with the phases of the grid voltages. If the modulation frequency is changed, an interference spectrum can be obtained which can be transformed back into a mobility spectrum with the aid of Fourier analysis. The method which was described by the authors as "Fourier Transform Ion Mobility Spectrometry" offers a theoretical ion duty cycle of 25%. With regard to an increase in signal-to-noise ratio the method failed to meet expectations, though. The method has not been successful and, according to our knowledge, is no longer used nowadays. However, due to its fundamental similarity with the method of this invention it is quoted here.

OBJECTIVE OF THE INVENTION

A method has to be found by which ions from a quasi-continuous ion supply can be utilized more efficiently in an ion mobility spectrometer than previously and can be used for a sensitive measurement of the mobility spectrum.

IDEA OF THE INVENTION

It is the basic idea of this invention to impress a fast temporal coding upon the drift of the ions by using the fast switching element already existent at the start of the drift section, whereby the coding affects each ion type of the ion flow in the drift section in the same manner and admits about 50% of all the ions on a statistical average. The coding is essentially binary and is achieved by blocking or admitting the ion flow at temporal intervals. The temporal intervals and the pauses in between are preferably of irregular length in order to generate a characteristic pattern. In other areas of spectroscopy such a coding has become familiar as a "Hadamard pattern" (usually as a fixed spatial pattern for a multi-slit device). The coding patterns of the various ion types are displaced toward one another due to the differing drift velocities during drift of the ions through the drift tube of the mobility spectrometer so that at the ion detector there is a complex-looking signal pattern of the ion current. A binary mathematical convolution of the coding pattern occurs with the mobility spectrum and a further convolution occurs with the diffusion profile. The diffusion profile looks like a bell-shaped Gaussian curve and is generated during drift by diffusion of the ions in the forward and reverse directions. The ion current is measured, digitized, and stored at the end of the drift section in its temporal sequence. This stored signal pattern (the time "sum curve " of the ion current) can then be decoded by the usual mathematical means for deconvolution, obtaining the mobility spectrum of the ions. If the intervals of blocking and admitting the ion current are of the same length in total, the ion current has a duty cycle of 50%.

The quality of the mathematical transformations for decoding is strongly dependent on the noise of the signal. It is therefore another basic idea of the invention to reduce the noise of the ion current signal by summation. This summation initially calls for a strict periodicity in the coding pattern of the switching times, whereby the length of the period must be at least equal to the drift time of the slowest ions in the spectrum. Summation then takes place cyclically via consecutive sections of the ion current signal which exactly correspond to this period length of the sample. From the summated ion current (the "sum curve" of the ion current) signal the spectrum can be decoded with much better accuracy of mass and intensity determination.

It is a further basic idea of the invention to also take account of the diffusion broadening in decoding and, through deconvolution with a bell-shaped Gaussian curve, to achieve a mobility spectrum which has higher resolution. The two mathematical deconvolutions (that with the impressed switching pattern and that with the diffusion curve), can be performed in a single deconvolution step.

The ion source, which operates here with a beta emitter, can also be operated with corona discharges or UV lamps.

Figure 2:
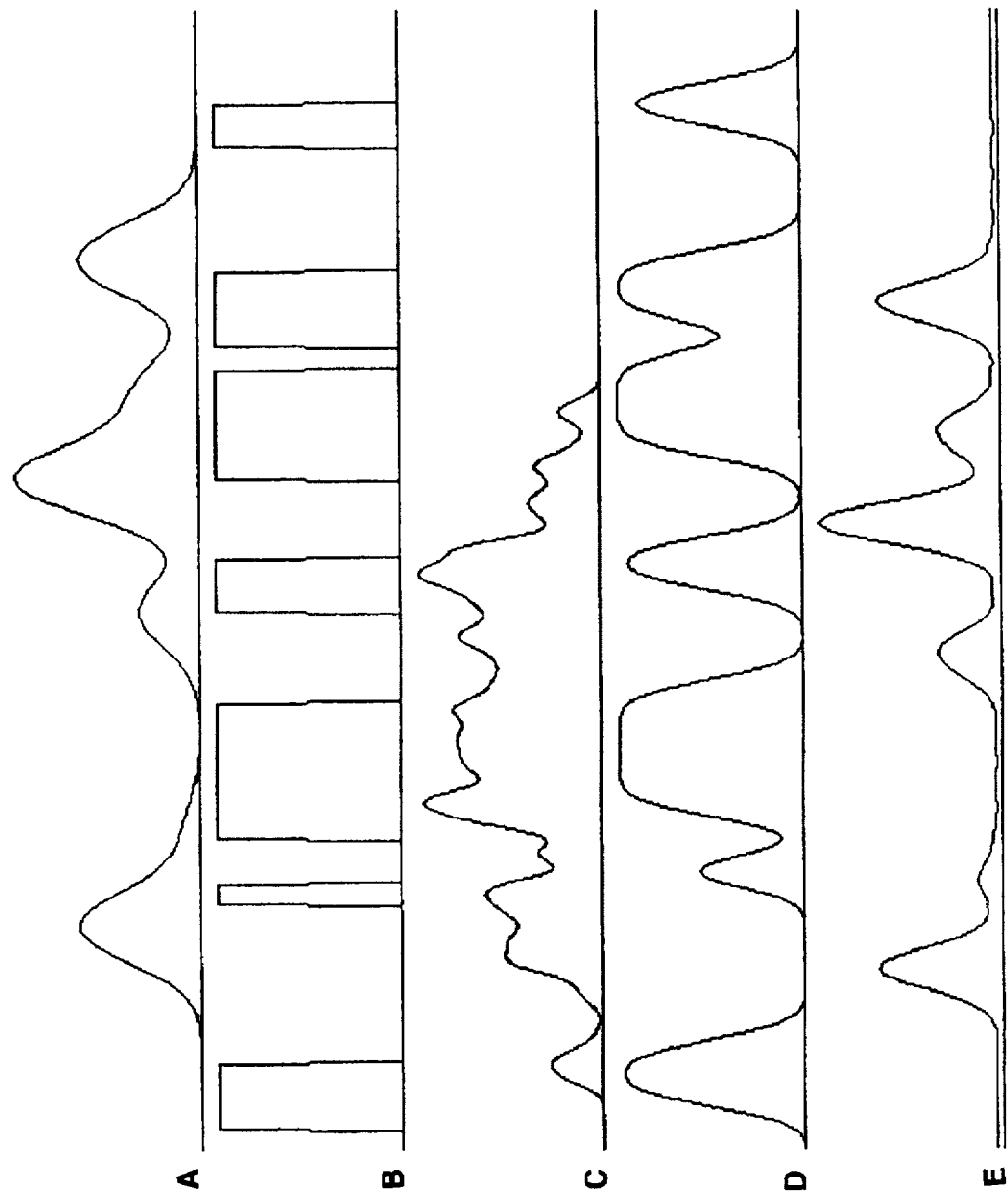

FIG. 2 illustrates the method of this invention using five curve traces A–E.

Curve trace A shows an ion mobility spectrum, as obtained by a short admission interval of about 200 microseconds. The curve trace is about 30 milliseconds long. It shows a total of 6 bell-shaped peaks, some of which overlap considerably though. The first bell-shaped-peak generally contains the remains of unspent water complex ions which act as reactant gas. The test substances usually have two bell-shaped peaks of various intensities, on the one hand the monomeric molecule ion and, on the other, the dimeric ion. Here the bell-shaped peaks of two substances are shown. The bell-shaped peaks are created by diffusion.

Curve trace B shows the switching pattern. Admission is opened if the switching pattern curve is not equal to zero.

Curve trace C shows the ion current signal which is created by superimposing the mobility spectrum on the switching pattern. Compared with the other ones the temporal length of this curve trace is compressed by a factor of 2 so the axis represents approximately 60 milliseconds. This signal has to be decoded.

Curve trace D shows a mathematically generated convolution of the switching pattern with an assumed Gaussian curve for the diffusion broadening. Diffusion broading has only been taken into account to the extent of 80% of the measured broadening because otherwise good deconvolution would not be possible. This curve is used for deconvolving the ion current signal from curve trace C.

Curve trace E provides the results of the deconvolution of curve C with the "apparatus function" D. It can be seen that curve E represents the mobility spectrum with a much improved resolution. Deconvolution was obtained by complex division of the Fourier-transformed curve C by the Fourier-transformed curve D with subsequent back transformation by an inverse Fourier transformation. By contrast with spectrum A, curve E seems slightly offset, which is due to the convolution of the switching curve with diffusion broadening.

PARTICULARLY FAVORABLE EMBODIMENTS

Figure 1:
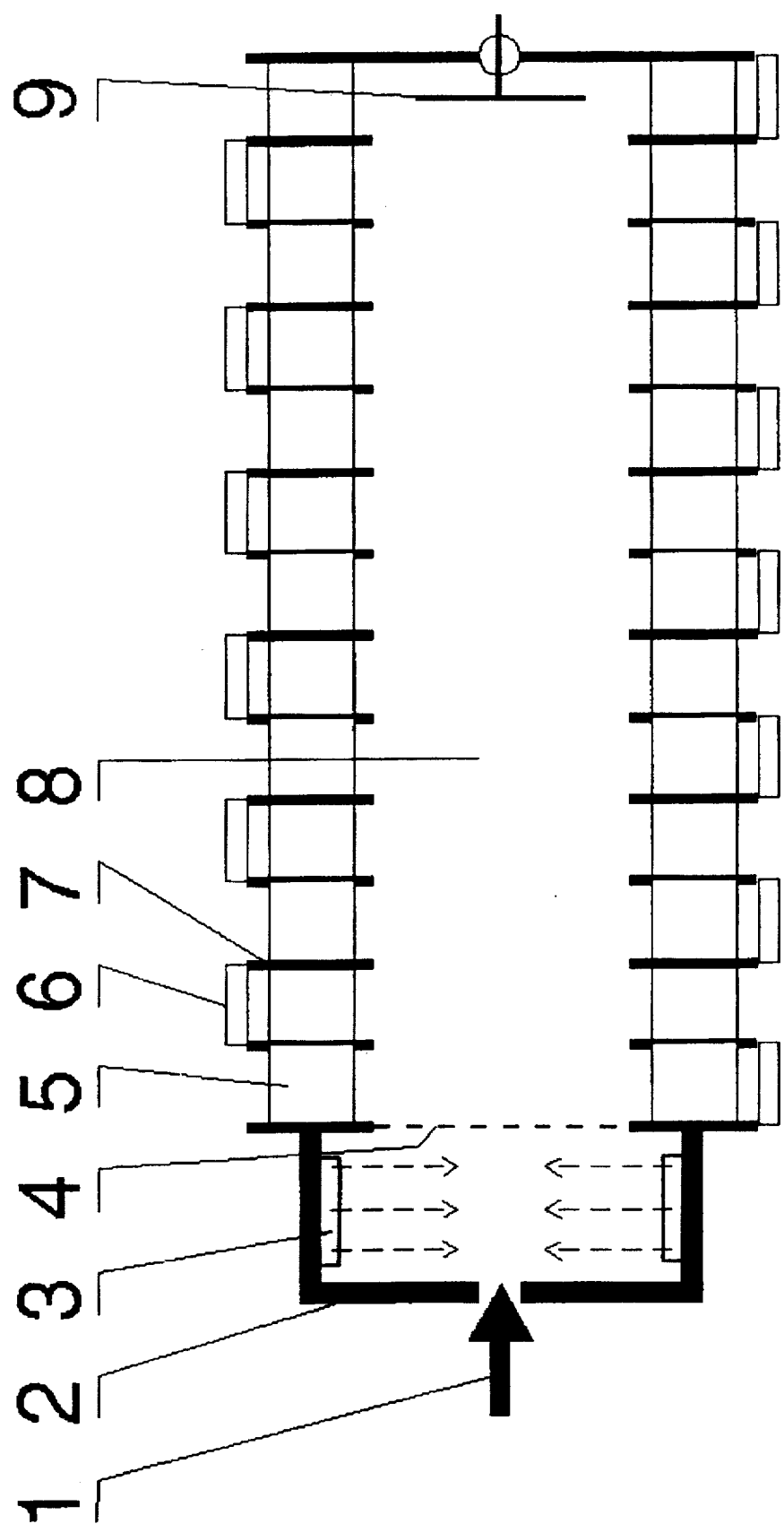
FIG. 1 shows a mobility spectrometer as is commercially available and as can be used for this invention without having to make any hardware modifications. Air with low contents of water and test substances (e.g. pollutants in the air) enter the ion source housing (2) along with the current of air (1). Some air molecules are ionized by the electrons of the beta emitter (3), which, for example, is made of $Ni^{63}$, and immediatly react in a complex manner with water molecules, forming complex ions $(H_2O)_n OH_3^+$. These serve as reactant gas ions for ionization of the pollutants. The ions in the ion source (2) drift toward the switching grid (4) where they are admitted in the temporal pattern of the switching intervals. The drift section (8) is made up of electrodes (7) which are separated from one another by isolators (5). They arc supplied with potentials, which generate a fairly uniform electrical field in the drift section (8), via a voltage divider, which comprises various resistors (6). The ions drift, drawn by this field, through the drift section (8) to the Faraday collector (9), where the time characteristic of the ion current is measured.

All the embodiments of the method can be performed in the apparatus based on FIG. 1, which is also used for the normal scanning of mobility spectra. The analysis substances, usually pollutants in air, enter the housing (2) of the ion source together with a slightly moist current of air (1). The nitrogen and oxygen ions generated by a beta emitter (3), for example $Ni^{63}$, initially react in complex reactions with water molecules, forming reactant gas ions. The latter react with the pollutant molecules. The ions of the pollutants and the remaining reactant gas ions are fed to the switchable grid (4) by means of a weak gas stream. The slow flow of ions generated in this way has in practice a diameter of Approx. 5 millimeters. This flow of ions passes through the switchable grid (4), which either admits or prevents the flow of ions.

The switching grid (4) consists of a very transparent grid made of closely spaced wires which alternately can be applied to different levels of potential. In this way the ions are fed to the wires, where they are discharged. The ion current is thus blocked and during the time of blocking the ions are destroyed. If the potential is temporally removed from the wires, grid (4) is switched to admission, the ions enter the drift section (8), and are drawn through the drift section by the electric field. The electric drawing field is generated by the electrodes (7), which are supplied with corresponding potentials by a chain of resistors (6). The electrodes (7) are separated by ceramic isolators (5). In the drift section (8) there is usually a light countercurrent of gas but its velocity is so low compared with the drift velocity that it is negligible. The gas current and its generation are not shown here.

The ions admitted to the drift section (8) then drift at their characteristic velocities through the drift tube, which is about 10 centimeters long, toward the ion detector (9), where they are measured as ion currents. The detector (9) is designed as a simple collector plate in order to impress no additional time smearing and acts as an extremely simple Faraday collector. The temporal characteristic of the ion current is termed "ion current signal" or "ion current time curve" below. If many different ion types are present, the impressed current intervals quickly blend in with the ion flow because the ions of different masses drift at different velocities. The ion currents arriving at the detector (9) are amplified, digitized, and are stored electronically as digitized ion current signals in the familiar manner as a sequence of values.

In the normal mode of an ion mobility spectrometer the ions are admitted with the switchable grid (4) only for a very short time of approx. 100 to 300 microseconds, and at the detector (9) the finished mobility spectrum is measured directly. FIG. 2 shows the curve trace A of such a mobility spectrum. The signal consists of various ion types, and some of the bell-shaped curves are considerably superimposed. The slowest ions of the mixture indicate the time which is required for a full scan. This time is termed "spectral period" below.

In operating this invention the switchable grid is operated according to a switching pattern, which is shown in curve trace B. The ions are admitted if curve trace B is not equal to zero. Curve trace C shows the ion current signal which arrives at detector (9) in the mode of operation based on this invention if the same ion mixture is used as in spectrum A.

If there were only one switchover in the spectral period, the ion currents would be integrated by summing at the leading edge of the admitting switched interval and would be integrated by subtracting at the tail end. The spectrum could then be obtained with relative ease by differentiation. There would be a relatively precise measurement of intensity but a relatively imprecise measurement of mobility because mobility is measured across the switchover edge, which occurs only twice.

If there are several switchovers in the spectral period, as shown in curve trace B of the figure, the ion current signal becomes much more complex but determination of the mobilities is much more accurate. This more complex ion current signal is shown in curve trace C of FIG. 2. However, ion current signal C can only be clearly decoded if the switchovers are not temporally uniform but produce a pattern which is clear and characteristic of the spectral period due to irregular lengths of interval, as illustrated in curve trace B.

In the simplest case the spectrum can be obtained from curve C by cross correlation with pattern B, at least as long as loopings of the switchover edges and diffusion divergence do not play a significant role.

If there are frequent switchovers, the spectrum can be obtained more efficiently by a mathematical deconvolution of curve C which can either use Hadamard, Fourier, Laplace or transformations. In doing so it is even possible to take the diffusion profile into account and also to partially eliminate it as a "function of the apparatus". Consequently it is possible to achieve levels of resolution for mobility measurement which are much better than those obtained by the normal method of mobility measurement Apparatus function D was calculated for this purpose as a mathematical convolution of switching function B with a Gaussian diffusion profile. Only about 80% of the full width of the measured bell-shaped diffusion profile was used because only then is it possible to achieve a good deconvolution. This "apparatus function" is shown in curve trace D of FIG. 2. Subsequent mathematical deconvolution of ion current signal C with apparatus function D produces mobility spectrum E, which, compared with the usual method of scanning, is clearly much improved in terms of peak resolution.

In this case deconvolution was performed in the familiar manner using Fourier transformations. Both the ion current characteristic C and apparatus curve D were subjected to Fourier transformation. Point by point the functions obtained were subjected to complex division and the quotient curve obtained was back-transformed by inverse Fourier transformation into mobility spectrum E.

However, the signal of the ion current may be very noisy. A considerable improvement can be achieved if the ion current characteristic is added up cyclically numerous times over the time of a scan. For this it is necessary to accurately repeat the temporal pattern of switching throughout the entire temporal period of scanning.

For this purpose it is favorable to digitally store the switching pattern and thus to control the electronic voltage supply to the ion beam switch. The quartz oscillator provides the basic pulse rate of control. The same quartz oscillator is also used to control the pulse rate of digitizing the measuring system and the pulse rate of storage. When the first period of ion current measurement has finished, output of the switching pattern exactly from the beginning and the measured values of the second period are added to the stored measured values of the first period. The measured values of the following period are also added. In this way a signal is obtained which is much less noisy and which provides excellent results after evolution.

If a measurement is taken every 80 microseconds, exactly 512 measured values are obtained during a period lasting 40.96 milliseconds. This number is particularly favorable for Fast Hadamard Transformations (FHT) or Fast Fourier Transformations (FFT).

If the measured values are each stored in a length of 4 bytes, a measurement can be accommodated in only 2 kilobytes of memory. Since for these calculations four memories of double the length are required, the spectra can be calculated in only 32 kilobytes of data memory. Some additional memory is required for substance libraries and substance identification. The programs can be kept in a read-only memory (ROM). In this way only one storage block of 64 kilobytes is required for the working memory (RAM) and a read-only memory of about the same size is required as program memory. These values are important because ion mobility spectrometers of this kind are essentially operated as portable battery-operated equipment weighing up to 1 or 2 kilograms.

I claim:

1. Method of measuring the mobility spectrum of ions in an ion mobility spectrometer, comprising an ion source, an ion drift section with an axial electric field, an ion detector for measuring the time curve of the ion current at the end of the ion drift section, and a switching element for ion admission between said ion source and said ion drift section, the method comprising the steps of:

(a) admitting the ions into the drift section with the switching element, wherein the switching element follows a temporal coding pattern consisting in admission and blocking times of irregular lengths of the ion admission, whereby the total admission times account for about 50% of the total time, and (b) obtaining the mobility spectrum from the time curve of the ion current measured at the detector by using mathematical deconvolution methods.

2. Method as in claim 1, wherein the deconvolution of the ion current time curve is performed by using the temporal coding pattern.

3. Method as in claim 1, wherein the admission and blocking times are short compared with the drift time of the slowest ions.

4. Method as in claim 1, wherein the mathematical deconvolution is performed by Hadamard transformations.

5. Method as in claim 1 wherein the mathematical deconvolution is performed by Fourier transformations.

6. Method as in claim 1, wherein the mathematical deconvolution also partially deconvolutes the diffusion profile.

7. Method as in claim 1, wherein (i) the coding pattern has a strong periodicity, the duration of the coding period being longer than the drift time of the slowest ions, (ii) the time curves of the ion current in consecutive coding periods are summed, value by value, to yield a sum curve, and (iii) the mobility spectrum is calculated from the sum curve by using mathematical deconvolution methods.

8. Method as in claim 7, wherein the mathematical deconvolution is performed by Hadamard transformations.

9. Method as in claim 7, wherein the mathematical deconvolution is performed by Fourier transformations.

10. Method as in claim 7, wherein the mathematical deconvolution also partially deconvolutes the diffusion profile.

* * * * *